(12) United States Patent
Akerstrom

(10) Patent No.: US 10,047,332 B2
(45) Date of Patent: Aug. 14, 2018

(54) BAG LOCKING MECHANISM

(71) Applicant: GE HEALTHCARE BIO-SCIENCES AB, Uppsala (SE)

(72) Inventor: Patrik Akerstrom, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 541 days.

(21) Appl. No.: 14/384,211

(22) PCT Filed: Mar. 15, 2013

(86) PCT No.: PCT/SE2013/050256
§ 371 (c)(1),
(2) Date: Sep. 10, 2014

(87) PCT Pub. No.: WO2013/137813
PCT Pub. Date: Sep. 19, 2013

(65) Prior Publication Data
US 2015/0056694 A1  Feb. 26, 2015

(30) Foreign Application Priority Data

Mar. 16, 2012 (SE) ..................................... 1250251

(51) Int. Cl.
*C12M 1/00* (2006.01)
*B01F 15/00* (2006.01)
(Continued)

(52) U.S. Cl.
CPC ......... *C12M 23/46* (2013.01); *B01F 11/0008* (2013.01); *B01F 11/0017* (2013.01);
(Continued)

(58) Field of Classification Search
CPC .............. B01F 11/0008; B01F 11/0017; B01F 15/00733; C12M 23/14; C12M 23/46; C12M 23/48; C12M 27/16
(Continued)

(56) References Cited

U.S. PATENT DOCUMENTS 5,639,050 A * 6/1997 Peterson ............. B65B 67/1205
220/495.08
6,461,853 B1 10/2002 Zhu
(Continued)

FOREIGN PATENT DOCUMENTS

JP         30007575      11/1999
WO    WO 2000/006676     2/2000
WO       WO0066706 A1   11/2000

OTHER PUBLICATIONS

JP Office Action dated Nov. 1, 2016 in corresponding JP Appl. No. 2015-500396.

*Primary Examiner* — Tan Le
(74) *Attorney, Agent, or Firm* — Wood IP LLC

(57) ABSTRACT

The invention relates to a bag locking mechanism comprising, a fixed locking means (106), provided with a first abutment surface (116), a movable locking means (108; 208), which is movable between a locking position and a releasing position, and a second abutment surface (118; 218) arranged on the movable locking means (108; 208). The fixed locking means (106) defines by its configuration, at least partly a restricted locking space (114), in which the movable locking means (108; 208) is movable between the locking and releasing position.

20 Claims, 6 Drawing Sheets

(51) Int. Cl.
*C12M 3/00* (2006.01)
*B01F 11/00* (2006.01)
*C12M 3/06* (2006.01)

(52) U.S. Cl.
CPC ....... *B01F 15/00733* (2013.01); *C12M 23/14* (2013.01); *C12M 23/48* (2013.01); *C12M 27/16* (2013.01)

(58) Field of Classification Search
USPC ............... 248/95, 99, 101; 435/288.7, 297.1, 435/305.1; 220/694
See application file for complete search history.

(56) References Cited

U.S. PATENT DOCUMENTS

| | | | |
|---|---|---|---|
| 8,458,866 B2* | 6/2013 | Hancz | B65F 1/06 24/555 |
| 2007/0292940 A1 | 12/2007 | Roll | |
| 2012/0260671 A1* | 10/2012 | Damren | B01D 5/0042 62/3.4 |
| 2015/0056694 A1* | 2/2015 | Akerstrom | C12M 23/14 435/305.1 |
| 2016/0152935 A1* | 6/2016 | Roosloot | C12M 23/14 435/297.1 |
| 2017/0036181 A1* | 2/2017 | Boettcher | B01F 11/0008 |

\* cited by examiner

BAG LOCKING MECHANISM

CROSS-REFERENCE TO RELATED APPLICATIONS

This application is a filing under 35 U.S.C. 371 of international application number PCT/SE2013/050256, filed Mar. 15, 2013, published on Sept. 19, 2013 as WO 2013/137813, which claims priority to application number 1250251-4 filed in Sweden on Mar. 16, 2012.

TECHNICAL FIELD

The present invention relates to bag locking mechanisms and in particular to a bag locking mechanism according to the preamble of claim 1. It further relates to bioreactors equipped with bag locking mechanisms.

Bag locking mechanisms are arranged to lock and fixate bags for different applications, such as e.g. in rocking tray bioreactors. When a bag is arranged on a rocking (wave) tray the bag locking mechanism holds the bag in a substantially fixed position on the tray when the tray moves back and forth.

BACKGROUND ART

Different types of bag locking mechanisms are known. In one known locking mechanism for hanging pillow bags vertically the bag is slid in place in a rail from one of side of the locking mechanism. When the bag contains fluid the bag is heavy and difficult to lift and handle. Therefore, it is difficult to both mount and to dismount the bag in the arrangement provided with such a known locking mechanism.

Another known bag locking mechanism is used in the tray of the WAVE™ bioreactor systems (GE Healthcare Life Sciences). This known mechanism has a movable clamp that is activated by an eccentric handle. When mounting the bag in the locking mechanism the movable clamp must be lifted by the operator mounting the bag. The lifting of the movable clamp and sliding the bag under the clamp must be performed simultaneously which is difficult for the operator. A similar clamp mechanism, for which the same considerations apply, is also disclosed in WO 00/66706 A1.

Document U.S. Pat. No. 6,461,853 discloses a locking mechanism for a flexible bag in a rigid, flat-bottom tray comprising of flexible elastic cables which have clamping devices at each end and hook-loop tape strips. When in use, the flexible bag is prepared on the tray and the elastic cables are straightened over the bag on the edges of the tray by using the clamps, and mount the straightened cable on the upper surface of the top web of the bag by using hook/loop tape strips. The straightened cable is capable of holding the top web of the bag in a fixed position.

Notwithstanding the existence of such prior art bag locking mechanisms, there is a need for an improved and more efficient locking mechanism that is easy, fast and safe to handle. The bag locking mechanism should also be easy to clean.

When the operator fixates and locks the bag in the bag locking mechanism it is important that the bag easily fits into the locking mechanism without jamming. The mounting of the bag into the locking mechanism must also be ergonomically correct for the operator and therefore the mounting must be easy, fast and safe to perform. Because the bags may contain fluid used in a chemical process it is also important that the equipment used is easy to clean.

SUMMARY OF THE INVENTION

An objective problem to be solved by the present invention is to achieve a bag locking mechanism which is easy, fast and safe to handle.

Another objective problem to be solved by the present invention is to achieve a bag locking mechanism which is easy to clean.

These objects above are achieved by a bag locking mechanism according to claim 1.

When the movable locking means is movable between the locking and releasing position in the restricted locking space defined by the fixed locking means a quick locking mechanism for the bag is achieved, which is self-locking when a force is applied. The locking mechanism makes it possible to attach and lock a bag by pushing it into the locking mechanism. When bag is to be removed from the locking mechanism a handle connected to the movable locking means releases the bag.

The invention accordingly comprises the features of construction, combination of elements, and arrangement of parts that will be exemplified in the description set forth hereinafter and the scope of the invention will be indicated in the claims.

In a second aspect the invention also discloses a bioreactor comprising a movable tray with at least one self-locking bag locking mechanism and a flexible plastic bag with at least one rod in a hollow seam provided at one side edge of the bag, wherein the bag is locked in the locking mechanism. The self-locking bag locking mechanism allows for fast, easy and safe handling even of large and heavy bags when loading and unloading the bioreactor. It also allows for easy cleaning of the bioreactor. These objectives are achieved by the bioreactor as described in the claims.

BRIEF DESCRIPTION OF THE DRAWINGS

Further aspects, advantages and features of the invention can be derived from the following detailed description of exemplary embodiments of the invention, with reference to the drawings.

DETAILED DESCRIPTION

Figure 1:
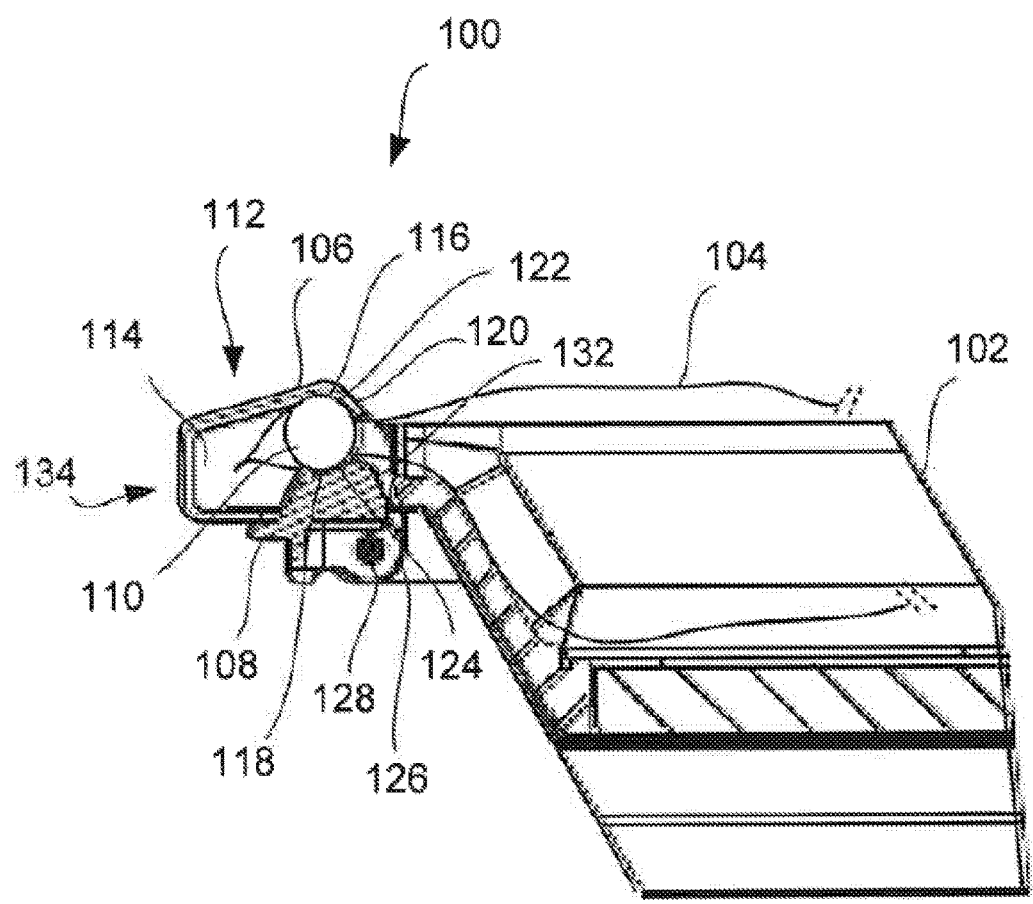
FIG. 1 shows a section view of a first embodiment of a bag locking mechanism according to the invention in a locking position.

FIG. 1 shows a first embodiment of a bag locking mechanism 100. In the disclosed first embodiment the locking mechanism 100 is integrated with a tray 102 for bags 104, but it is also possible to arrange the locking mechanism 100 according to the invention on other means, such as for example a wall or a shelf. The locking mechanism 100 comprises a fixed locking means 106 and a movable locking means 108, which together are arranged to lock and hold the bag 104. The bag 104 may be a flexible plastic bag, such as a disposable WAVE bag, a bioreactor bag, a filter bag, pillow bag or the like. Preferably, the bag is a disposable bag.

The movable locking means 108 is movable between a locking position and a releasing position. In FIG. 1 the movable locking means 108 is positioned in the locking position, in which a bag 104 is locked between the fixed and movable locking means 106, 108. The bag 104 may be of a substantially rectangular or square shape, and at least one rod 110, such as a substantially circular cylindrical rod, is contained in a hollow seam provided at one side edge 112 of the bag 104. The fixed locking means 106 defines by its configuration, at least partly, a restricted locking space 114, in which the movable locking means 108 is movable between the locking and releasing position. The movable locking means 108 may be movable into the restricted locking space 114 to reach the locking position and it may be movable out of space 114 to reach the releasing position.

The movable locking means 108 may in the locking position be located essentially inside the restricted locking space 114. In the releasing position, the movable locking means may be located either inside, partially inside or outside the restricted locking space 114. One advantage of having a locking means movable in a restricted locking space is that the locking mechanism can be manufactured without any protruding external clamps or other protruding parts, which can be a safety hazard on rocking trays. Another advantage is that cleaning of the mechanism is facilitated through the absence of external clamps or other protruding parts. The mechanism is easily manufactured and is capable of holding heavy liquid-filled bags of volumes up to at least 50 or 100 L on a rocking tray.

The fixed locking means 106 is provided with a first abutment surface 116 and the movable locking means 108 is provided with a second abutment surface 118. The fixed locking means 106 is provided with an abutment shoulder 120 on which the first abutment surface 116 is, at least partly, arranged. The first abutment surface 116 is configured with a first cavity 122 and the second abutment surface 118 is configured with a second cavity 124. The first and second cavities 122, 124 have a substantially equal shape. Preferably, the first and second cavities 122, 124 both have a radius, which substantially correspond to the radius of the rod 110 integrated in the bag 104. However, the first and second cavities 122, 124 may also have another shape which is adapted to receive the rod 110 integrated in the bag 104. The rod 110 abuts the first and second abutment surfaces 116, 118 and when a force is applied on the bag 104 in a direction away from the locking mechanism 100 the rod 110 will not leave the locking space 114 because of the configuration of the first and second abutment surfaces 116, 118 and of the configuration of the abutment shoulder 120 of the fixed locking means 106. The bag 104 with the rod 110 is thus engaged by the movable 108 and fixed 106 locking means and in consequence locked in place by the mechanism.

According to the first embodiment of the invention the movable locking means 108 is arranged to move pivotally between the locking and releasing positions. The movable locking means 108 is thus arranged on a shaft 128. Spring means 126 is arranged to urge the movable locking means 108 into the locking position. The spring means 126 can e.g. be a torsion spring, such as a helical torsion spring, which may be arranged such that the shaft 128 extends through the spring.

Figure 2:
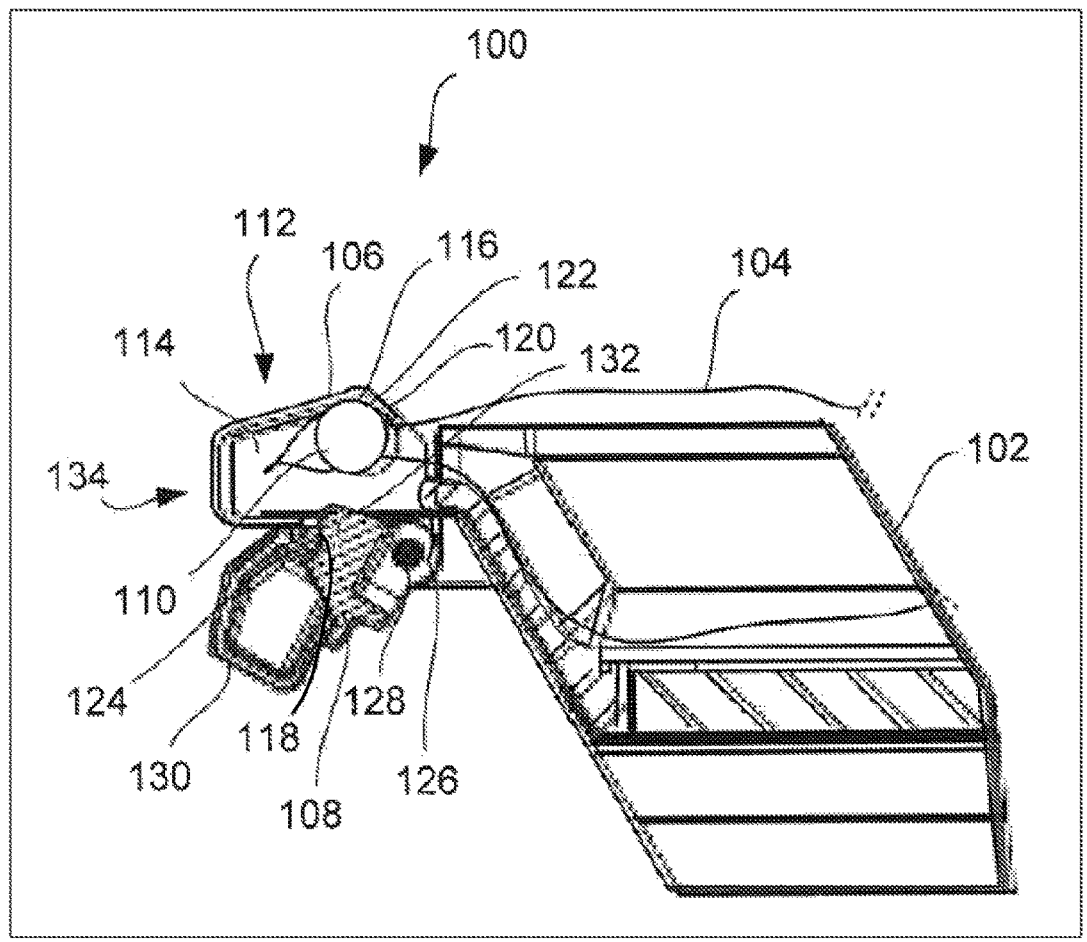
FIG. 2 shows a section view of the first embodiment of the bag locking mechanism according to the invention in a releasing position.

In FIG. 2 the movable locking means 108 has been moved to the releasing position. A handle 130 is arranged on the movable locking means 108, by which handle 130 the movable locking means 108 may be moved between the locking and releasing positions by a force applied on the handle 130. Preferably the movable locking means 108 is moved by an operator who manually moves the handle 130 using his hand. The rod 110 of the bag 104 may now leave the locking space 114. An advantage of this arrangement is that only light force needs to be applied to the handle in order to release the bag and the rod.

The movable locking means 108 is preferably provided with a control surface 132, on which a force may be applied to move the movable locking means 108 in a direction to the releasing position. When the bag 104 to be locked by the locking mechanism 100 is pushed against the control surface 132 the movable locking means 108 moves in a direction towards the releasing position and lets the bag 104 with rod 110 enter into the locking space 114 between the fixed and movable locking means 106, 108. When the bag 104 has entered into the space 114, between the fixed and movable locking means 106, 108, the bag 104 slides over the control surface 132 and onto the second abutment surface 118 of the movable locking means 108. The force of the spring means 126 will automatically return the movable locking means 108 to the locking position and the bag 104 is locked between the fixed and movable locking means 106, 108. In other words, movable locking means 108 is arranged to move in a direction towards the releasing position upon action on control surface 132 by entry of a bag 104 with a rod 110 into the restricted locking space 114. When the movable locking means 108 is arranged with spring means 126 to be urged into the locking position, a self-locking mechanism is achieved. An advantage of this is that the bag can easily be locked into position without operation of any handle. This leaves the operator with both hands free for positioning the bag and the rod, which is advantageous particularly for large and heavy bags.

Figure 3:
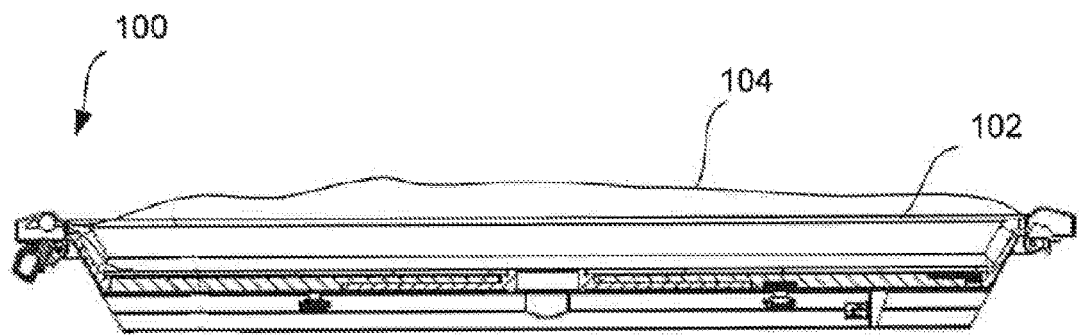
FIG. 3 shows a section view of a tray provided with the first embodiment of the bag locking mechanism according to the invention.

FIG. 3 shows the tray 102 in a section view. The tray 102 is provided with two locking mechanisms 100 according to the invention. The tray 102 has a substantially square shape and the two locking mechanisms 100 are arranged on opposite edges 134 of the tray 102. A substantially rectangular or square shaped bag 104 is placed on the tray 102 and locked on two opposite side edges 112 by the locking mechanism 100. In order to lock the bag 104 at opposed side edges 112 of the bag 104, at least one rod 110 per seam is contained in hollow seams provided at two opposed side edges 112 of the bag 104. The rods 110 are arranged substantially in parallel to the two opposite parallel edges 112 of the bag 104.

Figure 4:
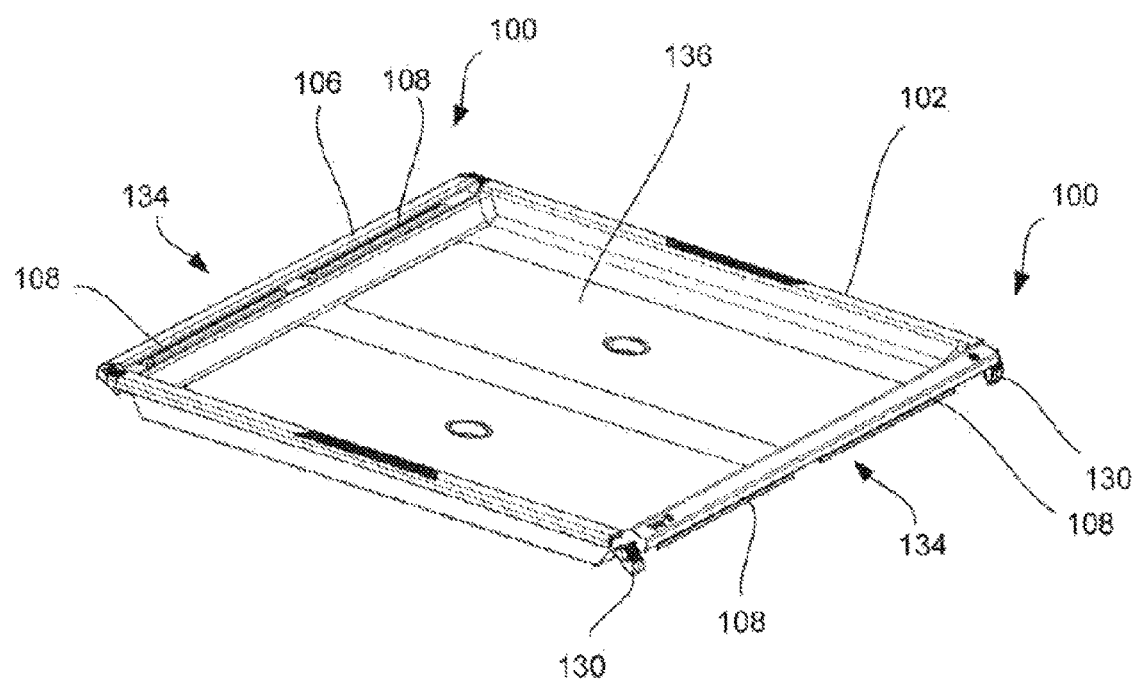
FIG. 4 shows a view in perspective of the tray in FIG. 3.

In FIG. 4 the tray 102 is disclosed in perspective, so that the upper side 136 of the tray 102 is exposed. The locking mechanisms 100 arranged on opposite side edges 134 of the tray 102 have a longitudinal extension and a length that substantially correspond to the length of the respective side edges 134 of the tray. The movable locking means 108 of the locking mechanisms 100 are in FIG. 4 arranged in pairs and may be individually movable by the handles 130 arranged in the corners of the tray 102. This configuration makes it possible to arrange two bags 104 in the tray 102 and each bag 104 may be locked to the tray 102 individually by a common fixed locking means 106, and an individually movable locking means 108. In FIG. 4 two movable locking means 108 on one side of the tray 102 are in a releasing position and two movable locking means 108 on the other side of the tray 102 are in a locking position.

Figure 5:
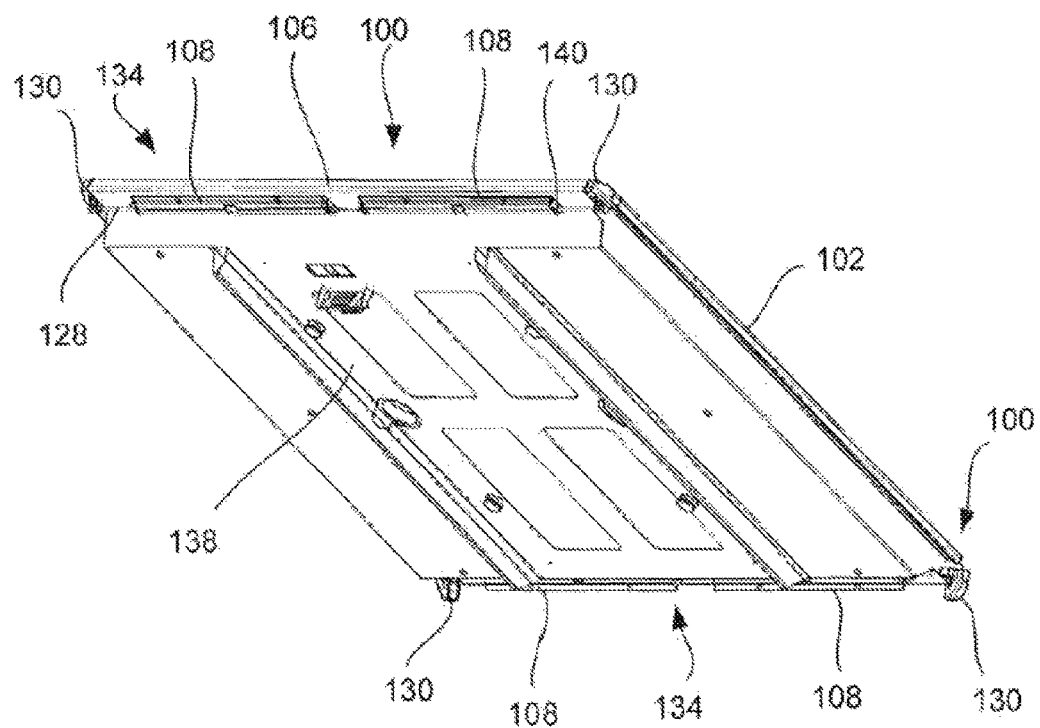
FIG. 5 shows a view in perspective of the tray in FIG. 3 in a different angle.

In FIG. 5 the tray 102 is disclosed in perspective from another direction, so that the underside 138 of the tray 102 is exposed. The locking mechanism 100 is provided with a holding means 140, which is arranged to hold the movable locking means 108 in the releasing position. When moving the movable locking means 108 to the releasing position the holding means 140 activates automatically when the handle 130 reaches an end position, in which the movable locking means 108 has reached the releasing position. The holding means 140 may be a friction lock or a snap lock. When a force is applied on the handle 130 which is larger than the friction force or snap force of the holding means 140 the movable locking means 108 moves in a direction to the locking position. The force applied on the handle 130 to release the movable locking means 108 from the than the friction force or snap force of the holding means 140 may be applied in a direction of the movement direction of the movable locking means 108, or in a direction perpendicular to said direction depending on the configuration of the holding means 140.

Figure 6:
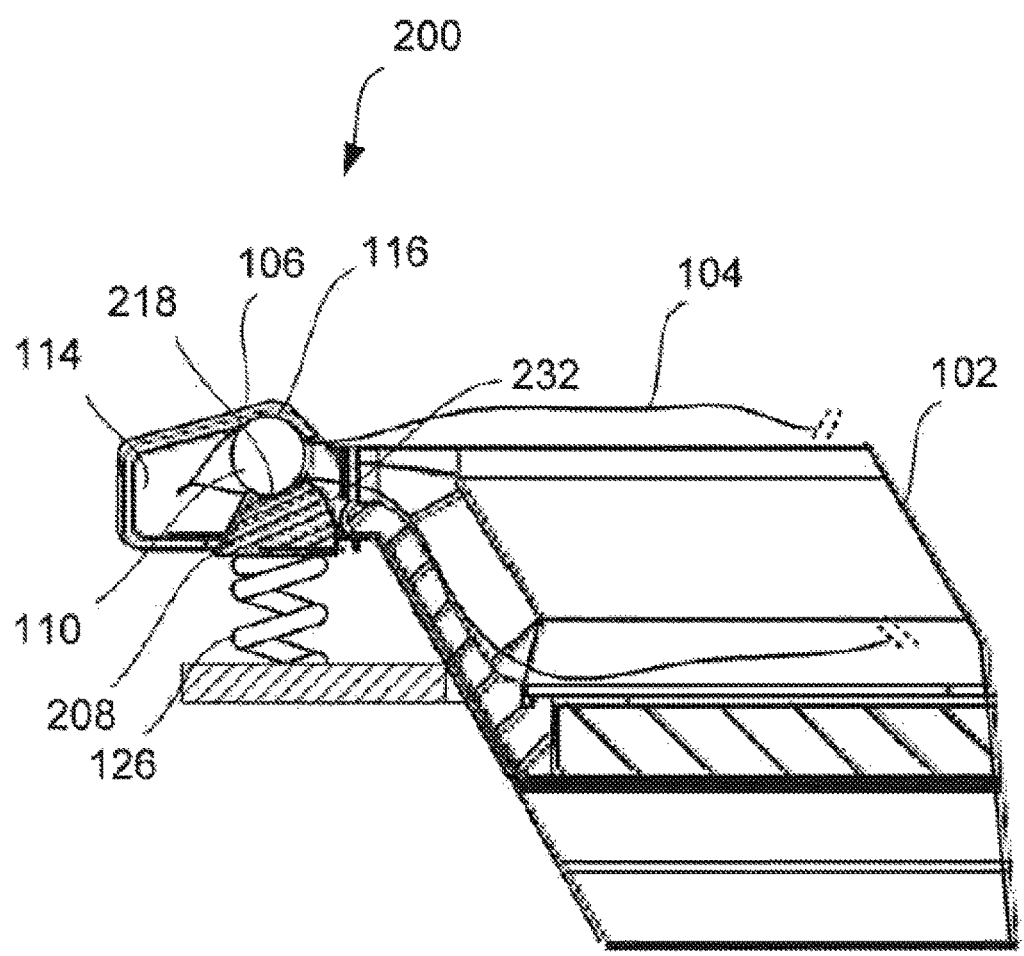
FIG. 6 shows a section view of a second embodiment of a bag locking mechanism according to the invention.

FIG. 6 shows a second embodiment of a locking mechanism 200 according to the present invention. In this second embodiment the movable locking means 208 is arranged to move substantially linearly between the locking and releasing positions. When the bag 104 to be locked by the locking mechanism 200 is pushed towards the control surface 232 the movable locking means 208 moves in a linear direction away from the fixed locking means 206 to the releasing position and lets the bag 104 enter into the locking space 114 between the fixed and movable locking means 106, 208. When the bag 104 has entered into the locking space 114, between the fixed and movable locking means 106, 208, the bag 104 with rod 110 slides over the control surface 232 and onto the second abutment surface 218 of the movable locking means 208. The force of the spring means 226 will automatically return the movable locking means 208 in a substantially linearly direction towards the fixed locking means 106 and to the locking position, so that the bag 104 with rod 110 is locked between the fixed and movable locking means 106, 208. Also in this embodiment it is possible to have a handle (not shown) for manual movement of movable locking means 208 to the releasing position.

In a second aspect of the invention, a bioreactor is disclosed, comprising a movable tray 102 which is equipped with at least one self-locking bag locking mechanism. The self-closing bag locking mechanism is arranged to receive a bag 104 with a rod 110 in a hollow seam and to lock it in place. It typically comprises a) a movable locking means, such as a latch, which is spring loaded and provides a first abutment surface and b) a non-movable locking means providing a second abutment surface. When receiving the bag with the rod, the movable locking means recedes and then moves back into a locking position by spring action, such that the bag and the rod are engaged by the first and second abutment surfaces of the movable and non-movable locking means. The mechanism may also comprise a handle 130 for manual movement of the movable locking means to a releasing position. The self-locking bag locking mechanism can be a bag locking mechanism 100;200 as described in any of the embodiments above.

The bioreactor can also comprise a flexible plastic bag 104 locked in at least one of the locking mechanisms, wherein the plastic bag has at least one rod 110 in a hollow seam provided at one side edge 112 of the bag 104. As described above, the bag with the rod can be inserted in the locking mechanism and locked between the first and second abutment surfaces. The bag can advantageously be equipped with one or more ports for introduction of cell culture media, cells, nutrients, gases and other reagents. In an advantageous embodiment, the tray has two locking mechanisms at opposing sides of the tray and the bag has two hollow seams provided at opposing side edges of the bags, with one rod inserted in each hollow seam. The side edges of the bag, with the rods, can then be inserted in and locked in the locking mechanisms to fix the bag in position. During cell cultivation the tray is moved to provide agitation and the bag will thus be prevented from sliding on the tray. After the cultivation is finished, the handles of the locking mechanisms can be acted upon to release the bag. In a specific embodiment the tray is arranged to pivot around an axis (not shown), which allows agitation by rocking.

The invention claimed is:

1. A self-locking mechanism for retaining a bag in place wherein the bag comprises at least one rod along one side edge of the bag, the mechanism comprising,
   a fixed locking means, provided with a first abutment surface;
   a movable locking means, which is movable between a locking position and a releasing position,
   a spring means configured to move the movable locking means from the releasing position to the locking position; and
   a second abutment surface arranged on the movable locking means,
   wherein the fixed locking means defines by its configuration, at least partly a restricted locking space where the rod can be inserted, in which the movable locking means is movable between the locking and releasing position,
   wherein the first abutment surface is configured with a first cavity in the fixed locking means and the second abutment surface is configured with a second cavity in the movable locking means, and
   wherein loading the rod of the bag against the second abutment surface triggers the self-locking mechanism which self-locks the bag through force of the spring means.

2. The locking mechanism according to claim 1, wherein the movable locking means is movable into the restricted locking space to reach the locking position and movable out of space to reach the releasing position.

3. The locking mechanism of claim 1, wherein the movable locking means in the locking position is located essentially inside the restricted locking space, with the first cavity and the second cavity sandwiching the rod.

4. The locking mechanism of claim 1, wherein the fixed locking means is provided with an abutment shoulder on which the first abutment surface is, at least partly arranged.

5. The locking mechanism of claim 1, wherein the first and second cavities have a substantially equal shape.

6. The locking mechanism of claim 1, wherein the first and second cavities have a radius which substantially correspond to the radius of the rod of the bag.

7. The locking mechanism of claim 1, wherein the movable locking means is arranged to move pivotally between the locking and releasing positions.

8. The locking mechanism of claim 1, wherein the movable locking means is arranged to move substantially linearly between the locking and releasing positions.

9. The locking mechanism of claim 1, wherein the locking mechanism is absent of any protruding external clamps or other protruding parts.

10. The locking mechanism of claim 1, wherein a handle is arranged on the movable locking means, by which handle the movable locking means may be moved between the locking and releasing positions by a force applied on the handle.

11. The locking mechanism of claim 1, wherein the movable locking means is provided with a control surface, on which a force may be applied to move the movable locking means in a direction to the releasing position.

12. The locking mechanism of claim 1, further comprising a holding means arranged to hold the movable locking means in the releasing position.

13. The locking mechanism of claim 1, wherein the locking mechanism is integrated with a tray for bags.

14. The locking mechanism of claim 1, wherein the rod in a hollow seam provided at one side edge of the bag.

15. A bioreactor comprising a movable tray with at least one self-locking back locking mechanism, arranged to receive a flexible plastic bag having at least one rod in a hollow seam provided at one side edge of the bag, wherein said self-locking bag locking mechanism comprises;
   a fixed locking means, provided with a first abutment surface;
   a movable locking means, which is movable between a locking position and a releasing position,
   a spring means configured to move the movable locking means from the releasing position to the locking position; and
   a second abutment surface arranged on the movable locking means,
   wherein the fixed locking means defines by its configuration, at least partly a restricted locking space, in which the movable locking means is movable between the locking and releasing position,
   wherein the locking mechanism is absent of any protruding external clamps or other protruding parts when in the locked configuration, and
   wherein the self-locking mechanism will self-lock through force of the spring means upon loading the rod of the bag against the second abutment surface.

16. The bioreactor of claim 15, further comprising a plastic bag, wherein said bag is locked in the locking mechanism.

17. The bioreactor of claim 15, wherein said tray is arranged to pivot around an axis.

18. The bioreactor of claim 15, wherein the restricted locking space is where the rod is inserted,
   wherein the first abutment surface is configured with a first cavity in the fixed locking means and the second abutment surface is configured with a second cavity in the movable locking means, and
   wherein in the locking position, the movable locking means is located essentially inside the restricted locking space, with the first cavity and the second cavity sandwiching the rod.

19. The bioreactor of claim 18, wherein the first and second cavities have a radius which substantially correspond to the radius of the rod of the bag.

20. The bioreactor of claim 15, wherein the movable locking means is provided with a control surface, on which a force may be applied to move the movable locking means in a direction to the releasing position.

* * * * *